US00PP27962P2

(12) United States Plant Patent
Moen

(10) Patent No.: US PP27,962 P2
(45) Date of Patent: May 2, 2017

(54) ***GERBERA* PLANT NAMED 'GARSURPRISE'**

(50) Latin Name: *Gerbera hybrida*
Varietal Denomination: Garsurprise

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 93 days.

(21) Appl. No.: 14/545,053

(22) Filed: Mar. 19, 2015

(51) Int. Cl.
*A01H 5/02* (2006.01)

(52) U.S. Cl.
USPC ..... Plt./357

(58) Field of Classification Search
USPC ..... Plt./357
See application file for complete search history.

(56) References Cited

PUBLICATIONS

Florist Breeding & propagation Catalogue 2014/2015. website https://issuu.com/martinew/docs/website_catalogus. 5 pages.*

* cited by examiner

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Gerbera* plant named 'Garsurprise', characterized by its compact, broadly upright and uniformly mounding plant habit; dense and bushy appearance; numerous inflorescences with dark red purple-colored ray florets; upright and strong scapes; and good garden performance and relatively tolerant to cold temperatures.

1 Drawing Sheet

Botanical designation: *Gerbera hybrida.*
Cultivar denomination: 'GARSURPRISE'.

BACKGROUND OF THE INVENTION

The present invention relates to a new and distinct cultivar of *Gerbera* plant, botanically known as *Gerbera hybrida* and hereinafter referred to by the cultivar name 'Garsurprise'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination made during the spring of 2010 in De Kwakel, The Netherlands of a proprietary selection of *Gerbera hybrida* identified as code number 09T163, not patented, as the female, or seed, parent with a proprietary selection of *Gerbera hybrida* identified as code number 05T124, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2011.

Asexual reproduction of the new *Gerbera* plant by cuttings in a controlled environment in De Kwakel, The Netherlands since the summer of 2011 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garsurprise'. These characteristics in combination distinguish 'Garsurprise' as a new and distinct *Gerbera* plant:

1. Compact, broadly upright and uniformly mounding plant habit.
2. Dense and bushy appearance.
3. Numerous inflorescences with dark red purple-colored ray florets.
4. Upright and strong scapes.
5. Good garden performance and relatively tolerant to cold temperatures.

Plants of the new *Gerbera* differ from plants of the female parent selection in the following characteristics:

1. Plants of the new *Gerbera* have slightly larger inflorescences than plants of the female parent selection.
2. Plants of the new *Gerbera* and the female parent selection differ in ray floret color as plants of the female parent selection have red-colored ray florets.

Plants of the new *Gerbera* differ from plants of the male parent selection in the following characteristics:

1. Plants of the new *Gerbera* have slightly smaller inflorescences than plants of the male parent selection.
2. Plants of the new *Gerbera* and the male parent selection differ in ray floret color as plants of the male parent selection have purple-colored ray florets.

Plants of the new *Gerbera* can be compared to plants of the *Gerbera hybrida* 'Gardreams', disclosed in U.S. Plant Pat. No. 26,636. Plants of the new *Gerbera* differ from plants of 'Gardreams' in the following characteristics:

1. Inflorescences of plants of the new *Gerbera* have more ray florets than inflorescences of plants of 'Gardreams'.
2. Plants of the new *Gerbera* and 'Gardreams' differ in ray floret apex shape as ray florets of 'Gardreams' have broadly acute to obtuse apices.
3. Plants of the new *Gerbera* and 'Gardreams' differ slightly in ray floret color as plants of 'Gardreams' have lighter red purple-colored ray florets.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garsurprise' grown in a container.

DETAILED BOTANICAL DESCRIPTION

The aforementioned photographs and following observations and measurements describe plants grown during the autumn and winter in 15-cm containers in a glass-covered greenhouse in De Kwakel, The Netherlands and under cultural practices typical of commercial garden *Gerbera* production. During the production of the plants, day temperatures ranged from 10° C. to 16° C. and night temperatures averaged 10° C. Plants were six months old when the photographs were taken and 17 weeks old when the description was taken. In the following description, color references are made to The Royal Horticultural Society Colour Chart, 2007 Edition, except where general terms of ordinary dictionary significance are used.

Botanical classification: *Gerbera hybrida* 'Garsurprise'.

Parentage:

*Female, or seed, parent*.—Proprietary selection of *Gerbera hybrida* identified as code number 09T163, not patented.

*Male, or pollen, parent*.—Proprietary selection of *Gerbera hybrida* identified as code number 05T124, not patented.

Propagation:

*Type*.—By cuttings and by tissue culture.

*Time to initiate roots, by cuttings, summer and winter*.—About 3.5 weeks at temperatures about 20° C.

*Time to initiate roots, by tissue culture, summer and winter*.—About 2.5 to 3 weeks at temperatures about 20° C.

*Time to produce a rooted young plant, by cuttings, summer and winter*.—About 3.5 weeks at temperatures about 20° C. to 26° C.

*Time to produce a rooted young plant, by tissue culture, summer and winter*.—About five to six weeks at temperatures about 20° C.

*Root description*.—Fibrous; white in color.

Plant description:

*Appearance*.—Herbaceous perennials that are typically grown as container or garden plants; compact and uniformly mounding plant habit, broadly upright and roughly globular in shape; numerous leaves arranged in basal rosettes and outwardly arching; dense and bushy habit; inflorescences held above the foliar plane on erect and strong basal scapes; low vigor to moderately vigorous growth habit.

*Plant height, soil level to top of foliar plane*.—About 21.1 cm.

*Plant height, soil level to top of inflorescences*.—About 30.6 cm.

*Plant width*.—About 49.3 cm.

Leaf description:

*Arrangement*.—Alternate, simple.

*Length*.—About 22.3 cm.

*Width*.—About 9 cm.

*Shape*.—Narrowly ovate; runcinate to panduriform; slightly curved.

*Apex*.—Broadly acute.

*Base*.—Acuminate.

*Margin*.—Coarsely and irregularly angulate; sinuses divergent; undulate.

*Texture, upper surface*.—Sparsely pubescent along main vein.

*Texture, lower surface*.—Densely tomentose.

*Venation pattern*.—Pinnate.

*Color*.—Developing leaves, upper surface: Close to between 141B and 143A. Developing leaves, lower surface: Close to between 138B and N138B. Fully expanded leaves, upper surface: Close to 137B; venation, close to 144A to 144B. Fully expanded leaves, lower surface: Close to 147B; venation, close to N144D.

*Petioles*.—Length: About 6.4 cm. Diameter: About 4 mm. Texture, upper surface: Sparsely pubescent. Texture, lower surface: Moderately to densely pubescent. Color, upper surface: Close to 144A. Color, lower surface: Close to 144A; proximally tinged with close to 177C.

Inflorescence description:

*Appearance*.—Composite inflorescence form with oblanceolate-shaped ray florets; solitary inflorescences borne on upright and strong scapes and held above the foliar plane; ray and disc florets arranged acropetally on a capitulum.

*Fragrance*.—None detected.

*Flowering season*.—Plants begin flowering about three months after planting; under garden conditions in The Netherlands, plants flower from early spring to late summer; plants can be flowered year-round in the greenhouse.

*Inflorescence longevity*.—Depending on the temperature, inflorescences last about two to four weeks on the plant; inflorescences not persistent.

*Quantity of inflorescences*.—Freely flowering habit with about eleven open and developing inflorescences per plant at one time.

*Inflorescence buds*.—Height: About 2.2 cm. Diameter: About 2 cm. Shape: Flattened ovate. Color: Close to 143C; immature ray florets, close to 150C; towards the apex, close to N170C.

*Inflorescence size*.—Diameter: About 7.8 cm. Depth (height): About 2.6 cm. Diameter of disc: About 2.4 cm. Receptacle height: About 5 mm. Receptacle diameter: About 4 mm.

*Receptacle color*.—Close to NN155B.

*Ray florets*.—Quantity and arrangement: About 110 per inflorescence arranged in about three whorls. Orientation: About 55° from vertical. Length: About 4 cm. Width: About 9 mm. Shape: Oblanceolate. Apex:

Emarginate to praemorse. Base: Cuneate. Margin: Entire. Texture, upper surface: Smooth, glabrous; velvety; longitudinally ridged. Texture, lower surface: Smooth, glabrous; slightly velvety; longitudinally ridged. Color: When opening, upper surface: Close to 64B. When opening, lower surface: Close to 145C. Fully opened, upper surface: Close to 70A; color becoming closer to 71B and apex, close to 71D, with development. Fully opened, lower surface: Close to 145C to 145D tinged with close to 182D; color does not change with development.

*Disc florets*.—Quantity and arrangement: About 200 massed at center of receptacle. Length: About 1.7 cm. Width: About 3.5 mm. Shape: Tubular with upper two lobes free at the apex. Apex: Obtuse; upper 40%, free. Base: Lower 60%, fused. Margin, free lobes: Entire. Texture, upper and lower surfaces: Smooth, glabrous. Color, prior to opening: Apex: Close to 157A. Mid-section and base: Close to 157D. Color, when opening: Apex: Close to NN155A strongly tinged with close to 63C to 63D. Mid-section: Close to 155C. Base: Close to 157D. Color, fully opened: Apex: Close to NN155A strongly tinged with close to 63D. Mid-section: Close to 155C. Base: Close to 157D.

*Pappus*.—Quantity of hairs per floret: About 50. Length: About 7.5 mm. Diameter: Less than 1 mm. Texture: Soft. Color: Close to 183D.

*Phyllaries*.—Quantity and arrangement: About 60 per inflorescence arranged in about three whorls. Length: About 1.4 cm. Width (at base): About 3 mm. Shape: Lanceolate. Apex: Narrowly acute. Base: Cuneate. Margin: Entire. Texture, upper surface: Smooth, glabrous. Texture, lower surface: Moderately tomentose. Color, upper surface: Close to 144A. Color, lower surface: Close to 143C.

*Scapes*.—Length: About 26.1 cm. Diameter: Proximally, about 6 mm; distally, about 4 mm. Angle: About 10° from vertical. Strength: Strong. Texture: Densely tomentose. Color: Proximally, close to 144B tinged with close to 199A; distally, close to 143A to 143B.

*Reproductive organs*.—Androecium (present on disc florets only): Quantity per floret: Five. Filament length: About 7 mm. Filament color: Close to 155D. Anther shape: Lanceolate. Anther length: About 4 mm. Anther color: Close to 11A. Pollen amount: Scarce. Pollen color: Close to 15A. Gynoecium (present only on ray florets): Quantity per floret: One. Pistil length: About 1.25 cm. Stigma shape: Cleft. Stigma color: Close to 155A. Style length: About 1.15 cm. Style color: Close to NN155A moderately tinged with close to 76B. Ovary color: Close to 155A.

*Seeds and fruits*.—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance and to tolerate high temperatures about 35° C. and to be cold hardy to USDA Hardiness Zone 7.

It is claimed:

1. A new and distinct *Gerbera* plant named 'Garsurprise' as illustrated and described.

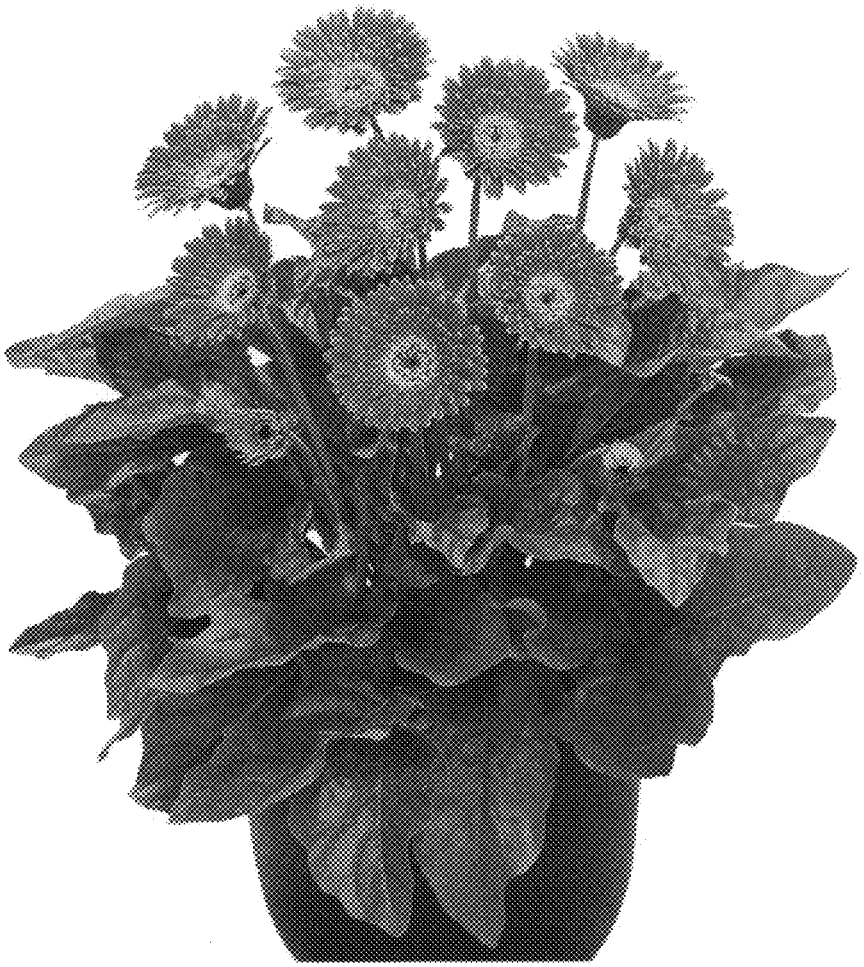

* * * * *